US012747455B2

(12) United States Patent
Ross

(10) Patent No.: US 12,747,455 B2
(45) Date of Patent: Sep. 29, 2026

(54) METHODS OF GENOMIC EVALUATION IN LIVESTOCK

(71) Applicant: Inguran, LLC, Navasota, TX (US)

(72) Inventor: Pablo Ross, College Station, TX (US)

(73) Assignee: Inguran, LLC, Navasota, TX (US)

( * ) Notice: Subject to any disclaimer, the term of this patent is extended or adjusted under 35 U.S.C. 154(b) by 1122 days.

(21) Appl. No.: 17/713,086

(22) Filed: Apr. 4, 2022

(65) Prior Publication Data

US 2023/0313233 A1 Oct. 5, 2023

(51) Int. Cl.

*C12N 15/877* (2010.01)
*C12N 5/073* (2010.01)
*C12Q 1/6876* (2018.01)
*G16B 20/00* (2019.01)

(52) U.S. Cl.

CPC ....... *C12N 15/8771* (2013.01); *C12N 5/0604* (2013.01); *C12N 5/0605* (2013.01); *C12Q 1/6876* (2013.01); *G16B 20/00* (2019.02)

(58) Field of Classification Search

None
See application file for complete search history.

(56) References Cited

U.S. PATENT DOCUMENTS 5,496,720 A 3/1996 Susko-Parrish et al.
5,843,705 A 12/1998 DiTullio et al.
6,258,540 B1 7/2001 Lo et al.
6,781,030 B1 8/2004 Baguisi et al.
7,592,503 B2 9/2009 Baguisi et al.
7,612,250 B2 11/2009 Overstrom et al.
7,893,315 B2 2/2011 Chung et al.
7,910,308 B1 3/2011 Beitz
8,338,098 B2 12/2012 Khatib et al.
10,179,938 B2 1/2019 Hayes et al.
2002/0032915 A1 3/2002 McEvoy et al.
2005/0014999 A1 1/2005 Rahe-Meyer
2005/0042595 A1 2/2005 Haas
2005/0118712 A1 6/2005 Tsai et al.
2005/0177883 A1 8/2005 Rebholtz et al.
2006/0294603 A1 12/2006 Forsberg et al.
2010/0304978 A1 12/2010 Deng et al.
2012/0004112 A1 1/2012 Lund et al.
2017/0275692 A1* 9/2017 Moreno ............... C12N 5/0605

(Continued)

FOREIGN PATENT DOCUMENTS

CN 109112160 B 8/2021
EP 3385394 B1 12/2021
WO 2002/009510 A2 2/2002

(Continued)

OTHER PUBLICATIONS

Ripley, et al. Equine fetal genotyping via aspiration of yolk-sac fluid at 22-28 days of gestation. Theriogeneology. 2020; 142:34-40. (Year: 2020).*

(Continued)

*Primary Examiner* — Allison M Fox
*Assistant Examiner* — Gina Pronzati
(74) *Attorney, Agent, or Firm* — Ryan Christensen; Hashim Rahman

(57) ABSTRACT

The invention encompasses methods for increasing genetic progress in livestock including the use of genomic evaluation of embryonic or fetal DNA obtained from allantoic fluid or cells therein.

15 Claims, 1 Drawing Sheet

| Embryonic/Fetal Age at Time of Fluid Coll. | GTPI (or JPI where indicated) | Volume Allantoic Fluid Collected (ml) |
|---|---|---|
| 40 | 2302 | 10.5 |
| 40 | 2285 | 12.5 |
| 40 | 2326 | 11.5 |
| 40 | | 10.5 |
| 46 | 2806 | 10.5 |
| 33 | 2428 | 12.5 |
| 33 | 2128 | 10 |
| 33 | 2363 | 12.5 |
| 39 | 2889 | 10 |
| 39 | 2793 | 11 |
| 36 | 2962 | 14 |
| 38 | 120 (JPI) | 10 |
| 39 | 2767 | 14 |
| 39 | 2898 | 13 |
| 38 | 2832 | 11 |
| 38 | 2937 | 11 |
| 66 | 146 (JPI) | 45 |
| 40 | | 11.5 |
| 40 | 2856 | 11.5 |
| 40 | 2984 | 6.5 |
| 40 | 2800 | 11 |
| 40 | 2862 | 10.5 |
| 40 | 2931 | 11.5 |
| 40 | 2849 | 11.5 |
| 40 | 2820 | 10 |
| 38 | 2741 | 11 |
| 38 | 3056 | 9 |
| 45 | 2893 | 11.5 |
| 45 | 2834 | 22 |
| 40 | 2267 | 13 |
| 40 | | 10.5 |
| 40 | 2396 | 12.5 |
| 37 | 2937 | 13 |
| 54 | 2396 | 12 |
| 39 | 2310 | 15 |
| 39 | 2424 | 15 |
| 39 | 2482 | 15.5 |

(56) References Cited

U.S. PATENT DOCUMENTS

| | | | | |
|---|---|---|---|---|
| 2019/0150412 | A1* | 5/2019 | Heuer | A01K 67/027 |
| 2020/0281173 | A1 | 9/2020 | Moreno et al. | |

FOREIGN PATENT DOCUMENTS

| | | | |
|---|---|---|---|
| WO | 2010020252 A1 | 2/2010 | |
| WO | 2010033969 A1 | 3/2010 | |
| WO | 2014063016 A1 | 4/2014 | |

OTHER PUBLICATIONS

Cooper, et al. Relationship of call rate and accuracy of single nucleotide polymorphism genotypes in dairy cattle. Journal of Dairy Science. 2013; 96(5):3336-39. (Year: 2013).*
International Search Report and Written Opinion issued on Jul. 26, 2023 in related PCT Application No. PCT/US2023/017297.
Bousquet and Blondin, "Potential Uses of Cloning in Breeding Schemes: Dairy Cattle," Cloning and Stem Cells, vol. 6, No. 2, abstract (2004).
Meuwissen et al., "Prediction of total genetic value using genome-wide dense marker maps," Genetics 157, 1819 1829 (2001).
Van Raden, "Efficient Methods to Compute Genomic Predictions," Dairy Science 91, 4414 4423 (2008).
Prather et al., "Nuclear Transplantation in Early Pig Embryos." Biol. Reprod 41:414-418, 1989.
Campbell et al., "Sheep Cloned by Nuclear Transfer From a Cultured Cell Line." Nature 380:64-66, 1996.
Wilmut et al., "Viable Offspring Derived From Fetal and Adult Mammalian Cells." Nature 385:810-813, 1997.
Szollosi et al., "Remodeling of Mouse Thymocyte Nuclei Depends on the Time of Their Transfer into Activated, Homologous Oocytes." J. Cell Sci. 91:603-613, 1988.
Czolowska et al., "Behavior of Thymocyte Nuclei in Non-Actived and Activated Mouse Oocytes." 1984.
Stice and Robl, "Nuclear Reprogramming in Nuclear Transplant Rabbit Embryos." Biol. Reprod 39:657-664, 1988.
Prather et al., "Nuclear Transplantation in the Pig Embryo: Nuclear Swelling." J. Exp. Zool. 225:355-358, 1990.
Collas and Robl. "Relationship Between Nuclear Remodeling and Development in Nuclear Transplant Rabbit Embryos." Biol. Reprod 45:455-465, 1991.
Smith and Wilmut, "Influence of Nuclear and Cytoplasmic Activity on the Development in Vivo of Sheep Embryos after Nuclear Transplantation." Biol. Reprod. 40:1027 1035, 1989.
Wells et al., "Production of Cloned Lambs from an Established Embryonic Cell Line: A Comparison Between In vivo- and in Vitro—Matured CytoPlasts." Biol. Reprod. 57:385-393, 1997.
Wells et al., "Production of Cloned Calves Following Nuclear Transfer with Cultured Adult Mural Granulosa Cells" Biol. Reprod. 60:996-1005, 1999.
Kato et al., "Eight Calves Cloned from Somatic Cells of a Single Adult" Science 282:2095-2098, 1998.
Prather et al., "Nuclear Transplantation in the Bovine Embryo: Assessment of Donor Nuclei and Recipient Oocyte" Biol. Reprod. 37:859-866, 1987.
Bondioli et al., "Production of Identical Bovine Offspring by Nuclear Transfer" Theriogenology 33:165-174, 1990.
Miller et al., "A Simple Salting Out Procedure for Extracting DNA from Human Nucleated Cells." Nucleic Acids Research. vol. 16 No. 3. 1988.
Biase et al., "Protocol for Extraction of Genomic DNA from Swine Solid Tissues." Genetics and Molecular Biology, No. 25, vol. 3, pp. 313-315 (2002).
Gaillard et al., "The Primary Structure of Bovine Satellite 1.715." vol. 9, No. 22, pp. 6069-6082. 1981.
Cibelli, J. B., et al., "Cloned Transgenic Calves Produced from Nonquiescent Fetal Fibroblasts." Science, 280:1256-1258 (1998).
Yong, Z. and L. Yuqiang, "Nuclear-Cytoplasmic Interaction and Development of Goat Embryos Reconstructed by Nuclear Transplantation: Production of Goats by Serially Cloning Embryos." Biol. of Reprod., 58:266-269 (1998).
Presicce and Yang, "Nuclear Dynamics of Parthenogenesis of Bovine Oocytes Matured In Vitro for 20 and 40 Hours and Activated With Combined Ethanol and Cycloheximide Treatment." Mol. Reprod. Dev., 37.61-68 (1994).
Bordignon & Smith, "Telophase Enucleation: An Improved Method to Prepare Recipient Cytoplasts for Use in Bovine Nuclear Transfer." Mol. Reprod. Dev., 49:29-36 (1998).
Bradshaw et al., "UV Irradiation of Chromosomal DNA and Its Effect Upon MPF and Meiosis in Mammalian Oocytes." Molecul. Reprod. Dev., 41:503-512 (1995).
Fulka and Moore, "Noninvasive Chemical Enucleation of Mouse Oocytes." Molecul. Reprod. Dev., 34:427-430 (1993).
Andreau, J. M. and Timasheff, S. N., "Tubulin Bound to Colchicine forms Polymers Different from Microtubules." Proc. Nat. Acad. Sci. 79:6753 (1982).
Obrig, T. G., et al., "The Mechanism by which Cycloheximide and Related Glutarimide Antibiotics Inhibit Peptide Synthesis on Reticulocyte Ribosomes." J. Biol. Chem. 246:174 (1971).
Duskin, D. and Mahoney, W. C., "Relationship of the Structure and Biological Activity of the Natural Homologues of Tunicamycin." J. Biol. Chem. 257:3105 (1982).
Scialli, A. R., et al., "Taxol and Embryonic Development in the Chick." Teratogen, Carcinogen, Mutagen 14:23 (1994).
Nishiyarna, I and Fujii, T., "Laminin-Induced Process Outgrowth from Isolated Fetal Rat C-Cells." Exp. Cell Res. 198:214 (1992).
Small, J. V., et al., "Coumarin—Phalloidin: a New Actin Probe Permitting Triple Immunofluorescence Microscopy of the Cytoskeleton." J. Cell Sci. 89:21 (1988).
Lee, J. C., et al., "Effects of Nocodazole of Structures of Calf Brain Tubulin." Biochem. 19:6209 (1980).
Weigel, K. A. "Genomic Selection and its Effects on Dairy Cattle Breeding Programs." Proceedings of 9th WCGALP, 2010.
Gao et al. Multilineage potential research of bovine amniotic fluid mesenchymal stem cells. Int. J Mol Sci Feb. 28, 2014 vol. 15 No. 3 pp. 3698-3710.
Holstein Foundation. Understanding Genetic and the Sire Summaries [online] Jan. 2015 [retrieved Dec. 21, 2016]. Available on the internet:<http://wayne.osu.edu/sites/wayne/files/imce/Program_Pages/ANR/Events/study%20material%20sire%20directories.pdf>.
Da Silva et al. "Production of Bovine Embryos and Calves Cloned by Nuclear Transfer Using Mesenchymal Stem Cells from Amniotic Fluid and Adipose Tissue." Cell Reprogram Apr. 2016 vol. 18 No. 2 pp. 127-136.
Kadarmideen et al. "Genomic Selection of In Vitro Produced and Somatic Cell Nuclear Transfer Embryos For Rapid Genetic Improvement in Cattle Production." Anim. Reprod., v.12, n.3, p. 389-396, Jul./Sep. 2015.
Ponsart C et al. "Embryo Genotyping : From DNA Amplification To Field Implementation", Proceedings of The 28th Annual Meeting of The European Embryo Transfer Association; Saint Malo, France,; Sep. 7-8, 2012, Sep. 7, 2012 (Sep. 7, 2012), pp. 83-93.
Poothappillai Kasinathan et al: "Acceleration if Genetic Gain in Cattle By Reduction of Generation Interval", Scientific Reports, vol. 5, Mar. 2, 2015 (Mar. 2, 2015), p. 8674.
Yudin N S et al: "Application of Reproductive Technologies to Improve Dairy Cattle Genomic Selection", Russian Journal of Genetics: Applied Research, , vol. 6, No. 3, May 14, 2016, pp. 321-329.
Cornelissen et al. "Estimating Variance Components and Breeding Values for Number of Oocytes and Number of Embryos in Dairy Cattle Using A Single-Step Genomic Evaluation", Journal of Dairy Science, vol. 100, No. 6, Mar. 30, 2017. pp. 4698-4705.
Cenariu et al. "Evaluation of Bovine Embryo Biopsy Techniques According to Their Ability to Preserve Embryo Viability", Journal of Biomedicine and Biotechnology, vol. 45, No. 5, Jan. 1, 2012,pp. 351-355.
Fisher et al. "Potential for Genomic Selection of Bovine Embryos", Proceedings of The New Zealand Society of Animal Production, vol. 72, Jul. 2, 2012, pp. 156-158.

(56) References Cited

OTHER PUBLICATIONS

Campbell et al. "Cell Cycle Co-Ordination in Embryo Cloning by Nuclear Transfer." Reviews of Reproduction (1996) 1, 40-46.
Sinclair et al. "Healthy Ageing of Cloned Sheep." Nature Communications. Jul. 2016.
Melka et al. "Identification of Genomic Differences between Hanwoo and Holstein Breeds Using the Illumina Bovine SNP50 BeadChip." Genomics & Informatics vol. 9(2) 69-73, Jun. 2011.
Harris "Experiences with the Illumina High Density Bovine BeadChip." Interbull Bulletin No. 44. Aug. 2011.
Infinium Assay. Lab Setup and Procedures. 2008.
Kamimura, S. et al. "Determining Sex of the Bovine Fetus With Y-Chromosome Specific DNA Amplified by PCR in Fetal Fluid Aspirated By Transvaginal- Transuterine Ultrasound-Guided Amniocentesis." Proceedings, 18th World Buiatrics Congress: 26th Congress of the Italian Association of Buiatrics, Bologna, Italy, Aug. 29 Sep. 2, 1994 vol. 1: 265-268.
Melo et al. "Isolation of transfected fibroblast clones for use in nuclear transfer and transgene detection in cattle embryos." Genetics and Molecular Research 4 (4): 812-821 (2005).
Coleman, Joseph Dewey "Genomic Testing and Method R Variance Components Theory of Dairy Cattle." A Senior Project presented to the Faculty of the Dairy Science Department California Polytechnic University, San Luis Obispo in Partial Fulfillment of the Requirements for the Degree Bachelor of Science By Joseph Dewey Coleman Mar. 2012.
Nana Fan et al. "Piglets Cloned from Induced Pluripotent Stem Cells." Cell Research (2013) 23:162-166. Dec. 18, 2012.
Vanraden et al. "Invited Review: Reliability of Genomic Predictions for North American Holstein Bulls." J. Dairy Sci. 92:16-24. 2009.
Wiggans et al. "The Genomic Evaluation System in the United States: Past, Present, Future." J. Dairy Sci. 94 :3202-3211. 2011.
"Genomic Data Adds Value in Marketing Holstein Sires Globally" ICommunity Newsletter. Aug. 2014.
Form Geno, Description of National Genetic Evaluation Systems. Jun. 18, 2010.
Illumina product listing. 4-9-13ddd.
Weigel et al.; "Accuracy of Direct Genomic Values Derived from Imputed Single Nucleotide Polymorphism Genotypes in Jersey Cattle" pp. 5423-5435;J. Dairy Sci., vol. 93, No. 11, 2010.
Schefers, et al."Gnomic Selection in Diary Cattle: Integration of D Testing Into Breeding Programs"; pp. 4-9; Jan. 2012, vol. 2, No. 1, Animal Frontiers.
Mosca-Boidron, et al. "An Improved Method to Extract DNA from a 1 ml of Uncultured Amniotic Fluid from Patients at Less than 16 Weeks' Gestation"; pp. 1-10; Apr. 2013, vol. 8, issue 4; Plos One.
Kasinathan, et al.; "Acceleration of Genetic Gain in Cattle by Reduction of Generation Interval"; pp. 1-4, Mar. 2, 2015; Scientific Report.
Eiras, et al.; "Amniotic Cell Culture During Different Ages of Gestation for Karyotype Analysis in Bovine"; pp. 291-295; Braz. J. vet. Res. Anim. Sci. 2000, Sao Paulo, vol. 37, n. 4.
Taniguchi et al.; "Establishment of a Method for Collective Bovine Fetal Cells from Amniotic Fluid by Transvaginal Aspiration"; Abstract No. 27; WCAP 2008, Cape Town, South Africa; Book of Abstracts.
Garrick et al. "Deregressing Estimated Breeding Values and Weighting Information for Genomic Regression Analyses." Genetics Selection Evolution 2009.
Haynes, B. J. et al. "Invited Review: Genomic Selection in Dairy Cattle: Progress and Challenges." J. Dairy Sci. 92:433-443, 2009.
Le Bourhis et al. 135 Breeding Values Concordance Between Embryos and Corresponding Calves Reproduction, Fertility and Development vol. 24, p. 180 (Year: 2011).
Ponsart et al. Reproductive technologies and genomic selection in dairy cattle Reproduction, Fertility and Development vol. 26, pp. 12-21 (Year: 2014).
Alkhoder et al., "A continuous genomic evaluation system for German Holsteins," Interbull Bull., 48, 100-104 (2014).
Peippo and Bredbacka, "Detection of bovine foetal DNA from amniotic fluid using polymerase chain reaction," Agricultural and Food Science in Finland, 5: 541-546 (1996).
Sargolzaei et al., "Results from the Boviteq embryo genotyping research project," Open Industry Session, 1-6 (Oct. 30, 2012).
Van Eenennaam et al., "Applied Animal Genomics: Results from the Field," Annu. Rev. Anim. Biosci., 2, 105-139 (2014).
Rossi et al., "Isolation and in Vitro Characterization of Bovine Amniotic Fluid Derived Stem Cells at Different Trimesters of Pregnancy," Stem Cell Rev and Rep, 10(5): 712-724 (first available online Jun. 7, 2014).
Wheeler et al., "Application of sexed semen technology to in vitro embryo production in cattle, " Theriogenology, 65: 219-227 (2006).
McClure et al., "SNP selection for nationwide parentage verification and identification in beef and dairy cattle," in Proceedings, International Committee For Animal Recording Technical Series, ed. Kowalski et al., (Krakow; Rome: ICAR; ), 175-181 (Jun. 2015).
Vasconcelos et al., "Factors potentially affecting fertility of lactating dairy cow recipients," Theriogenology, 65: 192-200 (2006).
Kamimura et al. "Determination of Bovine Fetal Sex By PCR Using Fetal Fluid Aspirated By Transv Aginal Ultrasound-Guided Amniocentesis" Theriogenology 47:1563-1569, 1997.
Akyuz et al. "The effectiveness of gender determination using polymerase chain reaction and radioimmunoassay methods in cattle", Theriogenology, vol. 73, No. 2, Jan. 15, 2010.
Holstein Foundation: "Understanding Genetics and the Sire Summaries", Jan. 1, 2015, https://wayne.osu.edu/sites/wayne/files/imce/Program Pages/ANR/Events/study material sire directories.pdf.
Liu et al. "Regulation of DNA methylation on EEF1D and RPL8 expression in cattle." Genetica (2017) 145:387-395.
Bombard et al. "Fetal RHD genotype detection from circulating cell-free fetal DNA in maternal plasma in non-sensitized RhD negative women." Prenat Diagn 2011; 31: 802-808.
Chrenek et al. "Sexing and Multiple Genotype Analysis From a Single Cell of Bovine Embryo." Theriogenology vol. 55, pp. 1071-1081, 2001.
Machaty et al. "Biopsy and Sex Determination By PCR of IVF Bovine Embryos." Journal of Reproduction and Fertility, vol. 98, pp. 467-470, 1993.
Lopes et al. "Splitting and Biopsy For Bovine Embryo Sexing Under Field Conditions" Theriogenology, vol. 56. pp. 1383-1392, 2001.
Polisseni et al. "Post-Biopsy Bovine Embryo Viability and Whole Genome Amplification In Preimplantation Genetic Diagnosis." Fertility and Sterility, vol. 93, No. 3, Feb. 2010.
Lopatarova et al. "Conception rate after sex determination and cryopreservation of D7 bovine embryos." Veterinarni Medicina, vol. 55, pp. 10-18, 2010.
Leibo et al. "Prenatal Diagnosis of Sex in Bovine Fetuses By Amniocentesis" Theriogenology vol. 33, No. 2. Feb. 1990. pp 531-552.
Hill, W., "Applications of Population Genetics to Animal Breeding, from Wright, Fisher and Lush to Genomic Prediction," Genetics 196(1): 1-16 (2014).
Office Action issued in counterpart Australian Application No. 2023250850, dated Nov. 7, 2025 (5 pages).
Supplementary European Search Report issued in counterpart European Application No. 23785231.4, issued Apr. 7, 2026 (8 pages).
Gutierrez-Reinoso, M. A., Aponte, P. M., & Garcia-Herreros, M. (2021). Genomic Analysis, Progress and Future Perspectives in Dairy Cattle Selection: A Review. Animals, 11(3), 599. https://doi.org/10.3390/ani11030599.
Nellis, S., Kester, K., Hoffman, P., & Weigel, K. (2012). Heifer Management Blueprints. University of Wisconsin—Madison. https://outagamie.extension.wisc.edu/files/2010/12/DairyHeiferGenomics101.pdf.

* cited by examiner

| Embryonic/Fetal Age at Time of Fluid Coll. | GTPI (or JPI where indicated) | Volume Allantoic Fluid Collected (ml) |
|---|---|---|
| 40 | 2302 | 10.5 |
| 40 | 2285 | 12.5 |
| 40 | 2326 | 11.5 |
| 40 | | 10.5 |
| 46 | 2806 | 10.5 |
| 33 | 2428 | 12.5 |
| 33 | 2128 | 10 |
| 33 | 2363 | 12.5 |
| 39 | 2889 | 10 |
| 39 | 2793 | 11 |
| 36 | 2962 | 14 |
| 38 | 120 (JPI) | 10 |
| 39 | 2767 | 14 |
| 39 | 2898 | 13 |
| 38 | 2832 | 11 |
| 38 | 2937 | 11 |
| 66 | 146 (JPI) | 45 |
| 40 | | 11.5 |
| 40 | 2856 | 11.5 |
| 40 | 2984 | 6.5 |
| 40 | 2800 | 11 |
| 40 | 2862 | 10.5 |
| 40 | 2931 | 11.5 |
| 40 | 2849 | 11.5 |
| 40 | 2820 | 10 |
| 38 | 2741 | 11 |
| 38 | 3056 | 9 |
| 45 | 2893 | 11.5 |
| 45 | 2834 | 22 |
| 40 | 2267 | 13 |
| 40 | | 10.5 |
| 40 | 2396 | 12.5 |
| 37 | 2937 | 13 |
| 54 | 2396 | 12 |
| 39 | 2310 | 15 |
| 39 | 2424 | 15 |
| 39 | 2482 | 15.5 |

METHODS OF GENOMIC EVALUATION IN LIVESTOCK

BACKGROUND OF THE INVENTION

When producing future generations of animals of the highest genetic merit or elite genomic value, a critical selection of potential breeding animals must be made. Only germplasm from the most elite animals can be harvested and used at the genetic nucleus level. Germplasm can include but is not exclusive to gametes such as sperm and oocytes, but also embryos, fetuses, neonates and somatic cells or tissues from living animals.

To that end, genomic testing in the livestock industry has become a valuable tool in evaluating young animals and in increasing genetic progress by increasing the accuracy of selection and decreasing the generation interval. Typically, young animals are genomically tested shortly after birth or as young adults, therefore requiring that significant resources be devoted to supporting the mother during fetal gestation even though the genetic merit of the offspring is unknown.

Embryo transfer is a procedure that follows fertilization (either in vitro or in vivo) and involves the transfer of one or more embryos, from a test tube or the biological mother, to a recipient animal for gestation and birth. Embryo transfer is another tool for increasing genetic progress, since it increases selection intensity by allowing the use of a smaller number of elite females as mothers of many offspring and may also decrease the generation interval in the case where female egg donors are made to ovulate sooner than they normally would be able to give birth. In the livestock industry, the major expense portion of any embryo transfer program is the cost and maintenance of recipient animals into which the embryos are placed for gestation, which may limit its application.

Cloning is yet another tool that can be used to increase genetic progress by increasing the accuracy of selection. See Bousquet and Blondin, "Potential Uses of Cloning in Breeding Schemes: Dairy Cattle," Cloning and Stem Cells, vol. 6, no. 2, abstract (2004). Cloning can also be used to speed up genetic dissemination of genes from animals of exceptionally high genetic merit to the commercial population. Id. The applicability of cloning has to date been limited, however, due to the lag time before a cloned animal can participate in a breeding program. Id. at 193.

Accordingly, there is a need to increase genetic progress and/or genetic dissemination by increasing and improving the use of genomic testing, embryo transfer and cloning in the livestock industry, as well as to reduce the costs and maintenance associated with maintaining recipient animals used in embryo transfer.

SUMMARY OF THE INVENTION

One embodiment of the invention comprises a method of increasing the rate of genetic progress in a non-human mammalian population comprising obtaining one or more embryonic or fetal cells from within an allantois of an embryo or a fetus gestating within a female; extracting DNA from the one or more embryonic or fetal cells; genotyping the extracted DNA to obtain a genotype for the embryo or fetus; determining a genomic estimated breeding value (GEBV) or a genomic predicted transmitting ability (GPTA) using the genotype; and selecting the embryo or fetus as a parent, or to produce gametes, based on the determined GEBV or GPTA. In a further aspect of the embodiment, the one or more embryonic or fetal cells are obtained from the allantois within 60 days of the embryo's or fetus's conception, within 50 days of the embryo's or fetus's conception or within 40 days of the embryo's or fetus's conception. In another aspect, the one or more embryonic or fetal cells are obtained from the allantois 28 to 60 days after the embryo's or fetus's conception, 30 to 40 days after the embryo's or fetus's conception or 30 to 35 days after the embryo's or fetus's conception. In a more specific embodiment, the method further comprises a step of culturing the one or more embryonic or fetal cells or a step of cloning the embryo or fetus using one of the one or more embryonic cells or fetal cells. In certain specific embodiments, call rates for the genotype are greater than 80%, or greater than 90%.

Another embodiment of the invention comprises a method of estimating a production value, a genotypic value or a breeding value of a non-human mammalian embryo or fetus comprising: obtaining one or more embryonic or fetal cells from within an allantois of an embryo or a fetus gestating within a female; obtaining omics data comprising one or more features from the one or more fetal or embryonic cells; determining feature weights for the one or more features; determining an estimated production value, genotypic value or breeding value of the embryo or fetus based on the determined feature weights; and selecting the embryo or fetus as a parent, or to produce gametes, based on the determined estimated production value, genotypic value or breeding value. A more specific embodiment further comprises a step of producing offspring from the selected embryo or fetus; a step of isolating the one or more embryonic or fetal cells from the allantoic fluid; or a step of cloning the embryo or fetus using one of the one or more embryonic or fetal cells. In a more specific embodiment, the one or more embryonic or fetal cells comprise one or more stem cells. In another embodiment, the non-human mammalian embryo or fetus is a bovid. In a more specific embodiment of the method, the step of obtaining omics data comprises i) obtaining DNA, RNA, a protein or a metabolite from the one or more embryonic or fetal cells or ii) detecting a protein or a metabolite in the one or more embryonic or fetal cells. In an even more specific embodiment, the RNA is comprised of mRNA, pre-mRNA, tRNA, rRNA, ncRNA, lncRNA, miRNA, siRNA, snoRNA, piRNA, tsRNA or srRNA.

An additional embodiment of the invention comprises a method of increasing the rate of genetic progress in a non-human mammalian population comprising obtaining allantoic fluid from within an allantois of an embryo or a fetus gestating within a female; extracting DNA from the allantoic fluid; genotyping the isolated DNA to obtain a genotype for the embryo or fetus; determining a genomic estimated breeding value (GEBV) or a genomic predicted transmitting ability (GPTA) using the genotype; and selecting the embryo or fetus as a parent, or to produce gametes, based on the determined GEBV or GPTA. In a more specific embodiment, the allantoic fluid is obtained from the allantois within 60 days of the embryo's or the fetus's conception, within 50 days of the embryo's or fetus's conception or within 40 days of the embryo's or fetus's conception. In another embodiment, the allantoic fluid is obtained from the allantois 28 to 60 days after the embryo's or fetus's conception, 30 to 40 days after the embryo's or fetus's conception or 30 to 35 days after the embryo's or fetus's conception.

In yet another embodiment, the invention comprises a method of estimating a production value, a genotypic value or a breeding value of a non-human mammalian embryo or fetus comprising obtaining allantoic fluid from within an allantois of an embryo or a fetus gestating within a female; obtaining omics data comprising one or more features from the allantoic fluid; determining feature weights for the one or more features; determining an estimated production value, genotypic value or breeding value of the embryo or fetus based on the determined feature weights; and selecting the embryo or fetus as a parent, or to produce gametes, based on the determined estimated production value, genotypic value or breeding value. In a more specific embodiment, the allantoic fluid is obtained from the allantois within 40 days of the embryo's or fetus's conception.

BRIEF DESCRIPTION OF THE DRAWINGS

FIG. 1 provides the results of genotyping from embryonic and/or fetal cells obtained from allantoic fluid.

DETAILED DESCRIPTION OF THE INVENTION

The present invention is a novel method encompassing embryo transfer, obtaining an embryonic or fetal cell sample from an allantoic fluid sample during gestation, extracting DNA or other omics-related material from the cell sample or the allantoic fluid, performing a genomic analysis of the extracted DNA or other omics-related analyses and then cloning the embryo/fetus. In certain embodiments of the invention, the decision to clone an embryo or fetus is based on its genomic analysis or other omics-related analyses, including but not limited to its genomic estimated breeding value (GEBV) with respect to one or more traits. In an alternative embodiment of the invention, an embryo may be generated through a natural mating or artificial insemination of a female and the embryo gestates solely in the same female, i.e., embryo transfer is unnecessary.

Certain embodiments of the invention can be used to select against production of animals of inferior or detrimental genetic and/or genomic value, while selecting for the production of the most productive elite genotypes, with the highest call rates, available in a genetic nucleus system. Accordingly, certain embodiments of the invention utilize genomic tools, extensive genetic and genomic evaluation for production, health, fertility and other physiological traits based on analysis of single nucleotide polymorphism (SNP) data from historical reference information, then combine breeding genotypes in a molecular and biotechnology-based breeding program to maximize genetic progress in a line, herd or genetic nucleus. In certain embodiments, embryos are created in vivo and in vitro from elite females and bulls to produce offspring with the potential for the highest genetic merit. If necessary, these embryos are transferred into a highly screened and selected group of recipients maintained on recipient farms. The females carrying these high genetic and/or genomic value pregnancy are monitored during pregnancy, verified for fetal sex and then placed into rotation for genetic diagnosis through collection of allantoic fluid or cells therein. During the gestation of an embryo or fetus within its mother or a recipient animal, fluid and cell aspiration from the allantois is performed. This fluid is collected in a novel aspirate collection system and brought into the laboratory to be placed into cell culture. Aspirate and cells are analyzed by cellular assays and/or genomic approaches, the cells are continued in culture to confluence, passage, cryopreservation or productive use. After genomic evaluations, genetic information can be used to determine the developmental fate and production direction of any developmentally competent pregnancy. In certain embodiments, selected genotypes are placed into a component somatic cloning system to propagate the most elite lines of genotypes. Breeders of non-human mammalian species are focused on increasing the rate of genetic progress in a population (e.g., a line, herd or genetic nucleus), as well as on increasing the rate of genetic dissemination of superior genotypes. In furtherance of these goals, tools such as genomic testing (and other omics-related analyses), embryo transfer and cloning are being developed and utilized by breeders at various stages of animal production.

Embryo transfer is extensively used in the modern livestock industry. As noted above, the major expense portion of any embryo transfer program is the cost and maintenance of the recipient animals. Typically, however, these costs are offset by the value of the resulting animal, and generally, the higher the genetic merit of the resulting animal, the higher its commercial value. Accordingly, embryo transfer programs place an emphasis on the production of high genetic merit animals.

One aspect of the instant invention allows a breeder to ascertain the genetic merit of a fetus early in gestation. Terminating the pregnancies of low genetic merit fetuses then allows a breeder to either reduce the number of females (i.e., mothers or recipient animals) needed in their breeding or embryo transfer program, or alternatively, to increase the number of high genetic merit fetuses that can be produced using a given number of females (i.e., mothers or recipient animals) over a given period of time (thereby increasing selection intensity and the rate of genetic progress). In another embodiment, after ascertaining the genetic merit of a fetus, a breeder may decide to maintain the pregnancy but replace the female carrying the fetus with a new female; and in yet a further embodiment the new female is carrying a fetus.

Another aspect of the instant invention allows a breeder to clone high genetic merit embryos and fetuses early in gestation and without harming the embryo or fetus. Specifically, fetal cells or tissue obtained for ascertaining genetic merit (via collection of allantoic fluid for example) are used to produce clones via somatic cell nuclear transfer.

Embryo Production In Vivo and In Vitro

In certain embodiments of the invention, embryos may be produced in vivo by traditional methods for synchronized supernumerary follicle production, artificial insemination (AI) and scheduled non-surgical transvaginal catheterized intrauterine embryo recovery. In other aspects of the invention, in vitro produced embryos may be produced in the laboratory by non-typical harvest of oocytes, in vitro fertilization (IVF) and embryo culture methodologies.

In peripubertal heifers, prophase I immature cumulus oocyte complexes (COCs) are recovered from live standing females by using ultrasound guided transvaginal oocyte recovery (TVOR) system, also referred to as ovum pickup (OPU). In prepubertal heifers, ultrasound guided laparoscopic OPU is employed for COC recovery. When immature COCs are brought into the laboratory, they are placed into typical in vitro maturation (IVM) culture system where the most developmentally capable oocytes undergo spontaneous and programmed meiosis. After an overnight culture period, those oocytes that progress through meiosis I (and accordingly shed their second polar body progressing to metaphase of the second meiotic division) and are morphologically normal (including an intact plasma membrane) are used in IVF. Mature oocytes from individual females are placed into traditional IVF drops and mated to specific sires, using highly screened and accurate sperm capacitation treatments and sperm concentration per oocyte fertilized. Zygotes (day 1) are placed into traditional co-culture system and cultured to uterine stages of development by day 7-8 of culture. Embryos are typically transported to a recipient heifer farm where they are non-surgically transferred. Prior to transfer, embryos may be biopsied or sampled for genetic screening and/or genomic evaluation. Within certain specific stages of embryo development, embryos can be dismantled and used in embryo multiplication procedures and/or cryopreserved for later use. Embryos destined for transfer to synchronized surrogate females are transported to the farm in culture and non-surgically transferred by traditional methods. In certain embodiments, the invention contemplates that recipient females are regularly checked by veterinarians and ongoing pregnancies are monitored on a regular and scheduled basis via transrectal real time ultrasonography.

By way of example only, the following oocyte maturation procedure, IVF procedure, in vitro culture procedure and co-culture procedure may be used with the invention.

Oocyte Collection. Collect slaughterhouse oocytes and wash 1× with about 3 mL Hepes washing media and with 1× with TCM-199 (Invitrogen, Carlsbad, CA)+10% Fetal Bovine Serum (FBS). Culture in maturation media for 22 hrs in a $CO_2$ incubator at 38.5° C. In one embodiment, the maturation media contains TCM-199, FBS, pyruvate, chorionic gonadotropin (e.g., Chorulon (Intervet, Summit NJ)), follicle stimulating hormone (FSH) (e.g., Folltropin (Bioniche, Belleville, Canada)), estradiol, and at least one antibiotic. In a further embodiment, Amikacin (Sigma-Aldrich, St. Louis, MO) can be used as the antibiotic. In another embodiment, the maturation media may also comprise luteinizing hormone.

In one embodiment, the maturation media may comprise 5-20 ml of TCM-199 Earl's; 0.5-2 ml of FBS (Thermo Fisher Scientific, Waltham, MA); 10-30 µl of pyruvate (prepared by adding 0.05-0.20 g of sodium pyruvate (Sigma-Aldrich, St. Louis, MO) to 5-20 ml of saline solution); 50-200 µl of chorionic gonadotropin (prepared by adding 5-20 UI of Chorulon (Intervet, Summit NJ) to 5-20 ml of TCM-199 Earl's); 5-20 µl of FSH (prepared by adding 0.001-0.01 g of Folltropin (Bioniche, Belleville, Canada) to 5-20 ml of TCM-199 Earl's); 5-20 µl of estradiol (prepared by adding 0.001-0.05 g of estradiol (Sigma-Aldrich, St. Louis, MO) to 5-20 ml of Ethanol (Sigma-Aldrich, St. Louis, MO)); and 10-30 µl Amikacin (prepared by adding 0.1-1 g Amikacin sulfate salt (Sigma-Aldrich) to 20-40 ml of saline solution). In alternative embodiments, the maturation media may comprise the aforementioned components using different volumes but in the same proportion to each other, e.g., in one embodiment, the maturation media may comprise 10-40 ml of TCM-199; 1-4 ml of FBS; 20-60 µl of sodium pyruvate, etc. In a further embodiment, the maturation media comprises the above preparations of TCM-199 Earl's, FBS, pyruvate, chorionic gonadotropin, FSH, estradiol and an antibiotic in the approximate ratio of 9:1:0.02:0.1:0.01:0.01:0.02 by volume, respectively.

In Vitro Fertilization. Trim away cumulus cells from matured oocytes. Transfer them to a fertilization dish and return to the $CO_2$ incubator. Thaw frozen semen straws using standard procedures, centrifuge in 8004, of Pure Sperm gradient (Nidacon, Molndal, Sweden), or a percoll or similar gradient at 2500 RPM for 10 minutes to remove egg components, glycerol and other debris. Remove supernatant, leaving a loose pellet of live sperm. Combine pellets using a small amount of fertilization media and repellet at 1500 RPM for 3 minutes. Carefully remove supernatant. Then gently mix the pellet. After determining the desired insemination dose, inseminate the oocytes by adding sperm to the oocytes, then culture in a dish and return to the $CO_2$ incubator for about 18-22 hours.

In Vitro Culture. Remove presumptive zygotes from the fertilization dish and transfer into a sterile 1.5 mL eppendorf tube. Allow zygotes to form a loose pellet and remove excess media to form a 1:1 ratio of pellet and solution. Rinse the eppendorf tube with TCM-199, place contents into a dish and wash with BSA media. Then culture presumptive zygotes (discard disfigured oocytes, as well as oocytes with yellow colored cytoplasm or vacuolated cytoplasm) in a dual gas incubator (5% $CO_2$, 5% O2) at 38.5° C. for about 48 hours.

Co-culture. Transfer cleaved zygotes to co-culture dishes comprising the cumulus cells from the mature oocytes and FBS media topped with mineral oil and incubate in a $CO_2$ incubator at 38.5° C. until needed.

Embryo Transfer

Although not necessarily required, certain embodiments of the invention encompass embryo transfer. Specifically, in some embodiments, embryonic or fetal cell samples are obtained from allantoic fluid obtained from within a recipient animal into which the embryo has been placed via embryo transfer. In other embodiments of the invention, embryo transfer is used to transfer a cloned embryo into a recipient. Any method known in the art may be used to transfer an embryo into a recipient, including any known surgical or non-surgical method. In alternative embodiments, embryonic or fetal cell samples are obtained from embryos or fetuses that are conceived and that gestate entirely in vivo.

The following surgical and non-surgical methods of embryo transfer are provided by way of non-limiting example only.

In cattle, an embryo can be transferred via mid-line abdominal incision, or a flank incision, to a recipient under general anesthesia. Recipients are placed in squeeze chutes that give access to either flank. The corpus luteum is located by rectal palpation and the flank ipsilateral to the corpus luteum is clipped, washed with soap and water, and sterilized with iodine and alcohol. About 60 ml of 2 percent procaine is given along the line of the planned incision. A skin incision is made about 15 cm long, high on the flank, just anterior to the hip. Muscle layers are separated, and the peritoneum is cut. The surgeon inserts a hand and forearm into the incision, locates the ovary, generally about 25 cm posterior to the incision, and visualizes or palpates the corpus luteum. The uterine horn is exteriorized by grasping and stretching with the thumb and forefinger the broad ligament of the uterus, which is located medial to the uterine horn. A puncture wound is made with a blunted needle through the wall of the cranial one-third of the exposed uterine horn. Using about 0.1 ml of medium in a small glass pipette (<1.5 mm outside diameter), the embryo is drawn up from the storage container. The pipette is then inserted into the lumen of the uterus, and the embryo is expelled. The incision is then closed, using two layers of sutures.

Alternatively, a non-surgical method may be used to transfer an embryo in cattle. First, it is necessary to palpate ovaries in order to select the side of ovulation, since pregnancy rates are lowered if embryos are transferred to the uterine horn contralateral to the corpus luteum. Recipients should be rejected if no corpus luteum is present or pathology of the reproductive tract is noted. The next step is to pass the embryo transfer device, e.g., a standard Cassou inseminating gun, through the cervix. The third step of non-surgical transfer is to insert the tip of the instrument into the desired uterine horn ipsilateral to the corpus luteum. The final step of the procedure is to transfer the embryo from a container, such as a straw, into the desired uterine horn using the transfer device.

Collection of Allantoic Fluid

Certain embodiments of the invention encompass methods of collecting allantoic fluid from an embryonic or fetal allantois. Once allantoic fluid is collected, a further aspect includes isolating embryonic or fetal cells from the allantoic fluid and performing genomic or other omics-related analyses on DNA or other material extracted from the embryonic or fetal cells or from the allantoic fluid itself. A specific embodiment includes extracting embryonic or fetal cell-free DNA from the allantoic fluid and performing genomic or other omics-related analysis on the DNA. Any method known in the art for collection of allantoic fluid may be used in the invention, including but not limited to trans-vaginal/trans-uterine collection using either ultrasound guided or manual puncture techniques. Additionally, allantoic fluid may be collected at any time during gestation in a mother or embryo transfer recipient, including but not limited to within 40, 50 or 60 days of the embryo or fetus's conception or 28 to 60, 30 to 40, 30 to 50, 35 to 45 or 30 to 35 days after the embryo's or fetus's conception.

By way of example, the following collection procedure may be used in the invention. One skilled in the art will know that variations on this method exist and that this method should not be construed to limit the functionality or scope of the current invention. This method is illustrative only.

Obtain a bovine mother, or recipient, with a gestating embryo or fetus. Administer standard caudal epidural anesthesia with 2% lidocaine. Raise the animals approximately 40 cm at the front using a platform in order to place the reproductive tract back towards the pelvis. Clean and disinfect the vulva region and inside of the vaginal vaults several times with iodine. Trans-rectally retract the uterus with the opposite hand and juxtapose the pregnant horn against the vaginal wall. Insert an ultrasound-transducer covered with a sterile sleeve into the vaginal vault with the aid of light lubrication approximately to the level of the cervix. Aspirate the allantoic fluid by intra-vaginal placement of a needle (Ø=1.3 mm, 68 cm length) installed within the body of the ultrasound-transducer and connected to a vacuum-tube blood collection assembly. Ultrasound scanner may be equipped with a 5.0 MHz convex type transducer approximately 1.6 cm wide and 58 cm long. Advance the needle through the vaginal and uterine walls by sharply moving the vacuum tube over a distance of about 3 to 4 cm. If the syringe plunger meets resistance, reposition the needle and take another aspirate. Transfer the aspirate to a sterile 10 ml test tube, placed on ice, and submit for genomic or other omic-related analysis. Confirm successful needle placement by direct observation of ultrasonography and allantoic fluid swirling within the vacuum tube. Embryonic or fetal viability may be assessed between 7 to 10 days after the aspiration procedure. Imaging of either independent fetal movement or heartbeat may be taken as proof of viability.

Another collection method in pregnant cattle encompasses the use of ultrasound-guided transvaginal oocyte recovery (TVOR) equipment, specialized fluid recovery tubing, and adapted filter collection system. In this example, in all cattle destined for the procedure for collection of allantoic fluid, pregnancy is confirmed by transrectal ultrasonography at specific periods after embryo transfer. Ultrasound-guided transvaginal oocyte recovery equipment is adapted and used to visualize the entire embryo, or fetus, and allantois during aspiration. Prior to fluid collection, the heifers are restrained in stocks and sedated prior to performing the fluid collection procedure. The veterinary staff performing the collection use complete sterile procedures, including powder-free nitrile-gloved hands and ethanol sterilization of equipment. To ensure that the area is free of contamination before insertion of the transducer, the rectum is emptied of feces, and under epidural anesthesia the vulva and rectal area of the cow are thoroughly cleaned and scrubbed. The disinfection step is completed by rinsing the vulva and rectal area with Betadine solution and the rinsing and spraying the cleaned area with 70% ethanol. The TVOR equipment is cleaned and sterilized with ethanol immediately prior to its introduction into the vagina and is fitted with a sterile stainless steel single-needle guide. The TVOR equipment is advanced into the vagina, positioned to the left or the right of the cervical os and by means of manipulation per rectum, the pregnant uterine horn is positioned against the probe, avoiding interposition of other tissue in the proposed needle path. The exact location of the allantois is determined by the recognition of fetal body parts, the amniotic, allantoic and chorionic membranes, and the uterine wall. When a non-echogenic area representing allantoic fluid is seen on the monitor screen, a sterile needle with a stylette is inserted within the needle guide and advanced penetrating through the vaginal wall, uterus and subsequent embryonic or fetal membranes. As soon as the tip of the needle is seen to have entered the embryonic or fetal fluid compartment, the stylette is withdrawn from the needle and the needle is placed inside the allantois of the fetus. An initial amount of allantoic fluid is aspirated into the tubing and flushed out of the tubing system to reduce or eliminate maternal contamination. Then 10-20 ml of allantoic fluid is aspirated. During the allantoic fluid collection, the pregnant uterine horn is held in the same position, and the exact location of the tip of the needle is guaranteed by its visualization on the ultrasound screen. When samples from more than one heifer are collected on the same day, the needle-guide is replaced by a sterile one, and the transducer is thoroughly cleaned and disinfected before being used on the next animal. After collection of allantoic fluid is completed in an animal, the collected fluid is placed on ice and transported back to the laboratory for analysis and/or further processing.

Isolating Cells from Allantoic Fluid

Embryonic or fetal cells, including fibroblasts, epithelial cells and mesenchymal stem cells (MSCs), used in the present invention may be obtained from allantoic fluid. For purposes of the invention, embryonic or fetal cells may be isolated from allantoic fluid by any method known in the art, e.g., by centrifugation followed by removal of the supernatant.

Embryonic or Fetal Cell Culture

One aspect of the invention encompasses culturing embryonic or fetal cells isolated from allantoic fluid. Cultured cells can in turn be used in various applications, including genotyping or other omics-related analyses and for producing clones. By way of example, the following culturing procedure may be used in certain embodiments of the invention. One skilled in the art will know that variations on this method exist and that this method should not be construed to limit the functionality or scope of the current invention. This method is illustrative only.

Embryonic or fetal cells are centrifuged (200 g, 10 min) at room temperature and the pellet is gently resuspended in Chang medium. Cells are plated into 100 mm gelatinized Petri dishes and left undisturbed. Media is changed every 3-4 days. After 2 weeks in culture, they are trypsinized to disperse cells and allow their growth in a monolayer. Cells are cultured at 37° C. in a humidified 5% $CO_2$ atmosphere. Cells are passaged at a ratio 1:4 every 5 days until they reach 80% confluence. For subsequent passages, the media is aspirated, washed with PBS, detached with 0.05% trypsine for 5 min at 37° C.

Isolation and Culture of Mesenchymal Stem Cells

In certain embodiments of the invention, a two-stage culture method may be used to isolate, culture, and enrich mesenchymal stem cells (MSCs) from allantoic fluid collected during gestation. Mammalian mesenchymal stem cells are presumptively multipotent cells that have the potential to differentiate into multiple lineages including bone, cartilage, muscle, tendon, ligament fat and a variety of other connective tissues. Morphologically, mesenchymal stem cells in their undifferentiated state are spindle shaped and resemble fibroblasts. Under specific culture conditions, mammalian MSCs have been induced to differentiate into adipocytes, osteocytes and neuronal cells.

The two-stage culture protocol comprises a first stage of culturing fetal or embryonic cells isolated from allantoic fluid, and a second stage of culturing mesenchymal stem cells. The method begins by setting up primary cultures using cytogenetic laboratory cell culture protocol. Non-adhering allantoic fluid cells in the supernatant medium are collected. For culturing mesenchymal stem cells, the non-adhering cells are centrifuged and then plated in a culture flask with an alpha-modified Minimum Essential Medium supplemented with fetal bovine serum. For mesenchymal stem cell growth, the culture is incubated with humidified $CO_2$.

By way of example, the following specific culturing procedure may be used in certain embodiments of the invention. One skilled in the art will know that variations on this method exist and that this method should not be construed to limit the functionality or scope of the current invention. This method is illustrative only.

For culturing fetal or embryonic cells isolated from allantoic fluid, set up four primary in situ cultures in 35 mm tissue culture-grade dishes using Chang medium (Irvine Scientific, Santa Ana, Calif.). Collect non-adhering cells in the supernatant medium on the 5th day after the primary cell culture and keep them until a completion of fetal chromosome analysis.

For culturing mesenchymal stem cells, centrifuge the tube containing the non-adhering cells, then plate them in 5-15 ml of alpha-modified Minimum Essential Medium (α-MEM) supplemented with 10-20% fetal bovine serum (FBS) and 1-20 ng/ml b-FGF in a 25 $cm^2$ culture flask and incubate at 37° C. with 5% humidified $CO_2$ for mesenchymal stem cell growth.

Flow cytometry, RT-PCR, and immunocytochemistry may be used to analyze the phenotypic characteristics of the cultured mesenchymal stem cells. Von Kossa, Oil Red O and TuJ-1 stainings may be used to assess the differentiation potentials of the mesenchymal stem cells.

The following additional culture method is presented by way of example only. The invention contemplates sterile technique, including being gloved with non-powder nitrile gloves to process amniotic fluid. In certain embodiments of the invention, the entire process is performed in a cell culture laminar flow biosafety cabinet and only food grade ethanol is used in washing gloved hands whenever needed or possible.

Fluid and fetal or embryonic cells isolated from allantoic fluid are aspirated by pipette into 15 ml conical tubes. The collection filter is rinsed with culture medium to remove any adhered cells and repeated as necessary to remove a maximal amount of cells from the filter. The conical tubes are centrifuged until a cell pellet is formed, supernatant is aspirated, and cells are resuspended in cell culture medium. The cell suspension is thoroughly mixed and pipetted into culture wells and/or dishes. Cell cultures are placed into a cell culture incubator and cultured at 38.7 C in 5% $CO_2$/air for 5 days undisturbed. On day 5 of culture, cell culture dishes are removed from culture and cell culture medium and any floating cells are aspirated and placed into 15 ml centrifuge tube. The remaining cells plated on the original cell culture dishes, primarily fetal fibroblasts and MSCs are fed with fresh culture medium and placed back into cell culture incubators and cultured until 80-90% confluent. After reaching confluency, the cells are lifted for passage and/or cryopreservation. The aspirated floating cells can be started in a specific cell culture or used in fetal diagnostic testing and/or genomic testing and profiling. Both original plated embryonic or fetal cell cultures and original floating cell cultures can be cultured for indefinite passaging and cryopreservation. Cryopreserved embryonic or fetal cell cultures can be warmed and passaged or used in cloning procedures.

DNA Extraction and Amplification

Another aspect of the invention encompasses genotyping fetal or embryonic DNA, including cell-free DNA. In one embodiment, once embryonic or fetal cells have been isolated from allantoic fluid, their DNA may be extracted and used for genotyping. For purposes of the invention, the term "embryonic or fetal cell(s)" includes both cells isolated directly from allantoic fluid and cells cultured from cells isolated from allantoic fluid. In an alternative embodiment, embryonic or fetal cell-free DNA may be extracted from allantoic fluid and used for genotyping. Any suitable technique known in the art for extraction of cell-free DNA may be used with the invention. In a specific embodiment, embryonic or fetal cells are first cultured and then the DNA of the cultured embryonic or fetal cells can be used for genotyping. Embryonic or fetal DNA is extracted and then amplified (via PCR) so that there is a sufficient amount of DNA for genotyping. The invention encompasses embodiments in which the amount of DNA extracted is very low, ranging from 1 ng/μl to 10 ng/μl (based on double strand DNA assays). Visualization using 1% agarose gels has shown the extracted DNA in some examples to be large, ≥23000 MW with little fragmented DNA.

For genomic analysis, approximately 1-200 ng of double stranded DNA should be extracted per sample DNA at concentration per sample of 1-50 ng/ul. In certain embodiments of the invention, only 1 ng/μl to 10 ng/μl of DNA are necessary for genomic analysis. In a particular embodiment, less than 15 ng of DNA total is necessary for genomic analysis. In some embodiments of the invention, the DNA is used in genotyping for parental verification and genomic evaluation. The genomic evaluation for production, health, fertility and other physiological traits utilized in certain embodiments of the invention is based on analysis of SNP data from historical reference population data determined by genome-wide association studies (GWAS). This evaluation of embryonic or fetal DNA also allows for rapid generation modeling by allowing selection of an embryo fetus as a parent for the next generation of matings. Cells in culture may remain in cell culture for passage and eventual harvest and cryopreservation for later diagnostic, cytogenetic and biological productive use such as cloning.

By way of example, the following DNA extraction and amplification procedure may be used in certain embodiments of the invention. One skilled in the art will know that variations on this method exist and that this method should not be construed to limit the functionality or scope of the current invention. This method is illustrative only.

Cells exposed to culture media often contain fetal calf serum. Due to high levels of DNase commonly found in fetal calf serum and the presence of cations that could catalyze the hydrolytic cleavage of phosphodiester linkage in DNA, an equal volume of a solution containing Tris-EDTA is added to the harvested cells to chelate cations essential for DNase activity. After adding the Tris-EDTA, the cell suspension is then stored in 1.5 ml microcentrifuge tubes at 4° C. until required for DNA extraction.

The 1.5 ml tubes containing cell suspension are spun at ≥10000×g in a microcentrifuge for 45 seconds to pellet cells. The suspension solution is pipetted off carefully so as to not remove pelleted cells. Approximately 50 μl of suspension solution is left in the tube. The tubes are then vortexed for 10 seconds to resuspend the cell pellets. 300 μl of Tissue and Cell Lysis Solution (Epicentre; Madison Wisconsin) containing 1 μl of Proteinase K (Epicentre; Madison Wisconsin) are then added to each tube and mixed. The tubes are then incubated at 65° C. for 30 minutes while making sure to vortex at 15 minutes. The samples are then cooled to 37° C. Afterwards 1 μl of 5 mg/μl RNase A (Epicentre; Madison Wisconsin) is added to to each sample and then mixed. The samples are then incubated at 37° C. for 30 minutes. The samples are then placed in a 4° C. cooler for 5 minutes. 175 μl of MPC Protein Precipitation Reagent (Epicentre; Madison Wisconsin) are then added to each sample, and the samples are then vortexed vigorously for 10-15 seconds. The samples are then centrifuged in order to pellet debris for 8 minutes at ≥10000×g. The supernatant is then transferred to a clean microcentrifuge tube. 600 μl of cold (−20° C.) isopropanol is added to the supernatant. Each tube is then inverted 30-40 times. The DNA is then pelleted by centrifugation for 8 minutes in a microcentrifuge at ≥10000×g. The isopropanol is poured off without dislodging DNA pellet. The pellet is rinsed once with 70% ethanol and then the ethanol is carefully poured off so as not to disturb the DNA pellet. The residual ethanol is then removed with a pipet, and the DNA pellet is allowed to air dry in the microcentrifuge tube. Once dried, resuspend the DNA pellet in 20 μl Tris-EDTA.

Genotyping DNA

In one aspect of the invention, extracted and/or amplified DNA from fetal or embryonic cells, including mesenchymal stem cells, may be genotyped using SNP arrays or chips, which are readily available for various species of animals from companies such as Illumina and Affymetrix, or alternatively, using any sequencing method known in the art. For purposes of the invention, the term “genotyping” includes, but is not limited to, obtaining SNP and/or copy number variation (CNV) data from DNA. For purposes of the invention, the term “genotype” includes, but is not limited to, SNP and/or copy number variation (CNV) data obtained from DNA. Low density and high density chips are contemplated for use with the invention, including SNP arrays comprising from 3,000 to 800,000 SNPs. By way of example, a “50K” SNP chip measures approximately 50,000 SNPs and is commonly used in the livestock industry to establish genetic merit or genomic estimated breeding values (GEBVs). In certain embodiments of the invention, any of the following SNP chips may be used: BovineSNP50 v1 BeadChip (Illumina), Bovine SNP v2 BeadChip (Illumina), Bovine 3K BeadChip (Illumina), Bovide LD BeadChip (Illumina), Bovine HD BeadChip (Illumina), Geneseek® Genomic Profiler™ LD BeadChip, or Geneseek® Genomic Profiler™ HD BeadChip.

In another aspect of the invention, extracted and/or amplified cell-free DNA from allantoic fluid may be genotyped using any method in the art. By way of example, matrix assisted laser desorption/ionization time-of-flight mass spectrometry (MALDI-TOF MS) can be used to genotype such extracted cell-free DNA.

Determining GEBVs from SNP Data

The basis, and algorithm, for using SNPs in determining GEBVs is found in Meuwissen et al., “Prediction of total genetic value using genome-wide dense marker maps,” *Genetics* 157, 1819 1829 (2001), which is incorporated by reference herein in its entirety. Implementation of genomic data in predictions for desirable traits is found in Van Raden, “Efficient Methods to Compute Genomic Predictions,” *Dairy Science* 91, 4414 4423 (2008), which is incorporated by reference herein in its entirety.

Livestock in the United States are often ranked using selection indexes that incorporate data related to various commercially important traits. With the advent of genomic testing, genomic data is now commonly used to predict these traits. To calculate an animal’s score for a genomic selection index, one must first calculate the animal’s GEBVs for each trait in the index, which can be accomplished using the teachings in Meuwissen et al. and VanRaden, above. Next, one determines the economic weight for each trait in the index. Finally, to determine the animal’s score for the selection index, multiply each trait’s GEBV by its economic weight and then sum all of these values together.

A genomic index commonly used in the United States for Holstein dairy cattle is the Genomic Total Performance Index (GTPI®), which is comprised of the following traits: protein; feed efficiency; dairy form; feet and legs composite; somatic cell score; daughter calving ease; fat; udder composite; productive life; fertility index; and daughter stillbirth. In certain embodiments, feed efficiency is equal to the dollar value of milk produced less feed costs for extra milk and less extra maintenance costs, and the fertility index is a function of heifer conception rate, cow conception rate and daughter pregnancy rate. A genomic index commonly used in the United States for Jersey cattle is the Jersey Performance Index (JPI). In other embodiments of the invention, GEBV is used to determine Genomic Predicted Transmitting Ability (GPTA).

By way of example, in addition to determining a GEBV for a trait, the presence or absence of any of the following diseases and/or traits can be detected using SNP data or genomic data: Demetz syndrome; white heifer disease; Weaver syndrome (haplotype BHW); haplotype HHD; haplotype HH1; lethal brachygnathia trisomy syndrome; haplotype HH0; bovine hereditary cardiomyopathy; bovine dilated cardiomyopathy; neuronal ceroid lipofuscinosis; bovine chondrodysplastic dwarfism; notched ears/nicked ears; idiopathic epilepsy; bilateral convergent strabismus with exophthalmos; haplotype BHP; haplotype HHP; haplotype JHP; neuropathic hydrocephalus/water head; congenital hypotrichosis and anodontia defect/ectodermal dysplasia; ichthyosis fetalis; lethal trait A46/bovine hereditary zinc deficiency; Marfan Syndrome; double muscling; multiple ocular defects; bovine ocular squamous cell carcinoma; pink tooth; posterior paralysis/hind-limb paralysis; haplotype BHM; bovine spongiform encephalopathy/mad cow disease; mule foot disease (haplotype HEIM); myophosphorylase deficiency; dropsy; black/red coat color (haplotype HBR; haplotype HEIR); BAND3 deficiency; Charolais ataxia; bovine spinal dysmyelination (haplotype BHD); Dun coat color in Dexter cattle; bovine familial convulsions and ataxia; bulldog calf; simmental hereditary thrombopathy; GHRD; renal tubular dysplasia (RTD)/chronic interstitial nephritis; Hereford white face; haplotype HHC; developmental duplications; black kidney; cardiomyopathy/Japanese black cattle; crooked tail syndrome; congenital pseudomyotonia; bovine hereditary arthrogyposis multiplex congentia; belted; Syndrome d'Hypoplasie Généralisée Capréoliforme; fawn calf syndrome; bovine neonatal pancytopenia; rat-tail syndrome; cheilognathoschisis; German White Fleckvieh syndrome; haplotype JH1; paunch calf syndrome; acorn calf disease/congenital joint laxity and dwarfism; haplotype HH2; haplotype HH3; haplotype HH4; Holstein bull-dog dwarfism; haplotype AH1; haplotype HH5; haplotype JH2; and lethal arthrogyposis syndrome.

Estimating Production Values, Genotypic Values or Breeding Values from Omics Data (Including Genomic, Transcriptomic and Metabolomic Data) Obtained from Cells Isolated from Allantoic Fluid or Allantoic Fluid Itself In addition to estimating breeding values from genomic data, one embodiment of the invention encompasses estimating production, genotypic or breeding values from omics data generally. "Omics data" may include, but is not limited to, genomic, proteomic, transcriptomic, epigenomic, microbiomic or metabolomic data. Omics data is believed to take into account complex epistatic interactions that are not necessarily captured by genomic data alone. In the context of the invention, a "breeding value" is comprised of the sum of all gene effects that are relevant for a particular trait; a "genotypic value" is comprised of the breeding value, plus all gene interaction effects (i.e., dominance and epistasis); finally, a "production value" is comprised of the genotypic value plus the permanent environmental effects for the individual, including constant features.

In one embodiment of the invention, omics data is derived or obtained from molecules (small or large) or any other substances (ions, elements, etc.) obtained or extracted from an embryonic or fetal cell, tissue sample or allantoic fluid, or detected in the cell, tissue sample or allantoic fluid. Both the presence and the quantity of such molecules or substances within a sample may be determined. Any known method in the art for detecting, measuring, quantifying or assaying molecules or other substances may be used with the invention, including but not limited to molecular hybridization, immunohistochemistry, real time quantitative PCR, quantitative reverse transcription PCR, blotting, nucleotide sequencing, protein sequencing, nuclear magnetic resonance spectroscopy, mass spectroscopy, liquid chromatography, gas chromatography and electrophoresis. In a specific embodiment, a transcriptome may be profiled using a microarray.

In a particular embodiment, transcriptomic, proteomic or metabolomic data can be derived from RNA, proteins or metabolites, respectively, found within a cell, tissue or allantoic fluid sample. In certain embodiments, a cell or tissue sample may be obtained from allantoic fluid in accordance with any of the methods described hereinabove. Such a cell sample may be cryopreserved and then subsequently thawed for extraction of DNA or RNA or to obtain proteins or metabolites for profiling or any molecules providing omics data.

In one embodiment of the invention, omics data comprises features. For example, for metabolomic data, each assayed or measured metabolite can constitute a feature. In one embodiment, a feature may simply comprise the presence or absence of a particular molecule or substance, e.g., the presence of a particular metabolite or transcript, or alternatively a feature may comprise the quantity of a particular molecule or substance, e.g., the quantity of a particular metabolite or transcript. For example, the quantity of glucose in a tissue or blood sample can comprise a feature.

These features from the omics data can be entered into a training model in which feature weights are obtained or estimated. Any suitable training model known in the art may be used with the invention. See for example, Westhues et al., "Omics-based hybrid prediction in maize," Theor. Appl. Genet. (2017) 130:1927-1939; Sharifi-Noghabi et al., "MOLI: multi-omics late integration with deep neural networks for drug response prediction," Bioinformatics (2019) 35:i501-i509; and Kim et al., "Multi-omics integration accurately predicts cellular state in unexplored conditions for *Escherichia coli*," Nature Communications (2016), DOI 10.1038/ncomms13090, pages 1-12. For example, the normalized relative quantity of metabolites or mRNA can form feature blocks. Every metabolite or mRNA may be used as one distinct feature that contributes to the prediction of the variable or trait of interest.

Generally, the phenotype or trait can be modelled as a function of the feature set:

$$y=f(z)+e,$$

where f( ) is any conceivable linear or non-linear function of the feature set in z that maps to y and e are the residuals.

One such function is a linear mixed model, in which a linear combination of feature covariables and weights result in the predicted phenotype:

$$y=Xb+Zu+e,$$

where X is an incidence matrix for fixed effects (intercept and structural components of a potential trial design), Z is a matrix of feature covariates and u a vector of feature weights.

The predicted phenotype or traits is then: $\hat{y}=Zu$.

These feature weights can then be used downstream for the prediction or calculation of production values, genotypic values or breeding values for animals or cell or tissue samples. For example, the variable or trait of interest that enters the training model may be breeding values. The predicted value using the feature weights will then also be a breeding value by design. The same is true for production of genotypic values. A production value can be predicted by using the raw phenotypic observations as dependent variables while employing the available features for the prediction of that phenotype.

With respect to genomic data, in various embodiments of the invention, genomic data may comprise DNA or RNA-related data obtained from oligonucleotide arrays or other hybridization assays, DNA sequence data or RNA sequence data. In a specific embodiment of the invention, genomic data may be obtained from whole or partial genome sequencing using any technique known in the art. In addition to obtaining genomic DNA sequences, in other embodiments of the invention, RNA may also be sequenced, including messenger RNA (mRNA), precursor mRNA (pre-mRNA), transfer RNA (tRNA), ribosomal RNA (rRNA), non-coding RNA (ncRNA), long RNA, including long non-coding RNA (lncRNA) and small RNA, including micro RNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). In addition to sequencing such molecules, it is also contemplated that real time quantitative PCR or quantitative reverse transcription PCR may be used to quantify DNA or RNA in a sample.

One embodiment of the invention therefore comprises a method of determining a production value, a genotypic value or a breeding value of a non-human mammalian embryo or fetus comprising obtaining omics data comprising one or more features from one or more embryonic or fetal cells obtained in vivo, i.e., in utero; calculating feature weights for the one or more features; calculating a production value, a genotypic value or a breeding value of the embryo or the fetus based on the calculated feature weights; selecting the embryo or fetus as a parent or to produce gametes based on the calculated production value, genotypic value or breeding value; and producing offspring from the selected embryo or fetus.

Cloning

An additional aspect of the invention encompasses cloning embryos and/or fetuses that have been genomically evaluated using the techniques disclosed herein. Cloning is generally understood to be the creation of a living animal/organism that is essentially genetically identical to the unit or individual from which it was produced. In those embodiments of the invention that encompass cloned embryos and/or fetuses, any method by which an animal can be cloned that is known in the art can be utilized. Thus, it is contemplated that cloned embryos and cloned fetuses are produced by any conventional method, for instance including the cloning techniques described herein, as well as those described in international patent application PCT/US01/41561. In one aspect of the invention, a basis for cloning an embryo or a fetus is its genomic merit. In a further aspect, the embryo or fetus's genetic merit is determined by genomic analysis as disclosed herein.

The following example of cloning is provided by way of example only.

Oocyte Enucleation. In vivo matured oocytes are collected from donor females. Oocytes with attached cumulus cells or devoid of polar bodies are discarded. Cumulus-free oocytes are divided into two groups: oocytes with only one polar body evident (metaphase II stage) and the activated telophase II protocol (oocytes with one polar body and evidence of an extruding second polar body). Oocytes in telophase II are cultured in M199+10% FBS for 3 to 4 hours. Oocytes that are activated during this period, as evidenced by a first polar body and a partially extruded second polar body, are grouped as culture induced, calcium activated telophase II oocytes (Telophase II-Ca+2) and enucleated. Oocytes that have not activated are incubated for 5 minutes in PBS containing 7% ethanol prior to enucleation. Metaphase II stage oocytes (one polar body) are enucleated with a 25-30 micron glass pipette by aspirating the first polar body and adjacent cytoplasm surrounding the polar body (approximately 30% of the cytoplasm) presumably containing metaphase plate.

Telophase stage oocytes are prepared by two procedures. Oocytes are initially incubated in phosphate buffered saline (PBS, $Ca^{+2}/Mg^{+2}$ free) supplemented with 5% FBS for 15 minutes and Cultured in M 199+10% FBS at 38° C. for approximately three hours until the telophase spindle configuration or the extrusion of the second polar body is reached. All the oocytes that respond to the sequential culture under differential extracellular calcium concentration treatment are separated and grouped as Telophase II-$Ca^{2+}$. The other oocytes that do not respond are further incubated in 7% ethanol in M199+10% FBS for 5-7 minutes (Telophase II-ETOH) and cultured in M199+10% FBS for 2 to 4 hours. Oocytes are then cultured in M199+10%/FBS containing 5 μg/ml of cytochalasin-B for 10-15 minutes at 38° C. Oocytes are enucleated with a 30 micron (OD) glass pipette by aspirating the first polar body and approximately 30% of the adjacent cytoplasm containing the metaphase II or about 10% of the cytoplasm containing the telophase II spindle. After enucleation the oocytes are immediately reconstructed.

Embryo Reconstruction. Pluripotent stem cells are harvested by trypsinizing (0.025% trypsin/0.5 mM EDTA) (Sigma) for 7 minutes. Single cells are resuspended in equilibrated M199+10% FBS supplemented with 2 mM L-glutamine, penicillin/streptomycin. The donor cell injection is carried out in the same medium as for enucleation. Donor cells are graded into small, medium and large before selection for injection to enucleated cytoplasts. Small single cells (10-15 micron) are selected with a 20-30 micron diameter glass pipette. The pipette is introduced through the same slit of the zona made during enucleation and donor cells are injected between the zone pellucida and the ooplasmic membrane. The reconstructed embryos are incubated in M199 30-60 minutes before fusion and activation.

Fusion and Activation. All reconstructed embryos (ethanol pretreatment or not) are washed in fusion buffer (0.3 M mannitol, 0.05 mM $CaCl_2$, 0.1 mM $MgSO_4$—, 9 mM $K2HPO_4$, 0.1 mM glutathione, 0.1 mg/ml BSA in distilled water) for 3 minutes before electrofusion. Fusion and activation are carried out at room temperature, in a chamber with two stainless steel electrodes 200 microns apart (BTX® 200 Embryomanipulation System, BTX®-Genetronics, San Diego, Calif.) filled with fusion buffer. Reconstructed embryos are placed with a pipette in groups of 3-4 and manually aligned so the cytoplasmic membrane of the recipient oocytes and donor CFF155-92-6 cells are parallel to the electrodes. Cell fusion and activation are simultaneously induced 32-42 hours post GnRH injection with an initial alignment/holding pulse of 5-10 V AC for 7 seconds, followed by a fusion pulse of 1.4 to 1.8 KV/cm DC for 70 microseconds using an Electrocell Manipulator and Enhancer 400 (BTX®-Genetronics). Embryos are washed in fusion medium for 3 minutes, then they are transferred to M199 containing 5 μg/ml cytochalasin-B (Sigma) and 10% FBS and incubated for 1 hour. Embryos are removed from M199/cytochalasin-B medium and co-cultured in 50 microliter drops of M199 plus 10% FBS with goat oviductal epithelial cells overlaid with paraffin oil. Embryo cultures are maintained in a humidified 39° C. incubator with 5% $CO_2$ for 48 hours before transfer of the embryos to recipient females.

The following alternative cloning procedure is presented by way of nonlimiting example only.

Remove COC's from maturation medium and rinse through one dish of warm TL Hepes (MOFA GLOBAL, Bovi Pro Oocyte Washing Medium with BSA at 3 mg/ml, filtered). Transfer the COC's into a hyaluronidase drop within the dish of TL Hepes. The cumulus cells of the COC's are stripped by hand, first by using a 200 μl gel loader pipet tip to remove the outer layers of cumulus, then by using a denudation pipet to remove the remaining cumulus cells. Those oocytes that are clean (no cumulus cells) are transferred to a second dish of warm TL Hepes. If there are eggs that still have cumulus cells attached, transfer those to another drop of hyaluronidase and finish hand stripping them, then transfer to the TL Hepes dish. The maturation rate (MO, mature oocyte) is determined by checking each viable oocyte for an extruded polar body (PB). Those eggs that are not mature need to be enucleated immediately.

To a nunc well, add 0.50 ml of Cyto B medium (2 ml TL Hepes and 1 µl Cytochalasin B (Sigma C-6762)) and 10 µl of Hoescht stain. Remove the oocytes from the maturation medium and rinse through warm TL Hepes, and then place the oocytes in the nunc well with the Hoescht stain for 15 minutes. At the end of the 15 minutes, rinse the oocytes through warm Cytochalasin B. Transfer to the lower drop of Cytochalasin B in a manipulation plate. Using the tip of a glass enucleation tip (25 µm inner diameter), pierce through the zona of an oocyte, carefully, bring your tip near to the chromosomes and slowly aspirate them out, taking as little cytoplasm as possible. When that oocyte is successfully enucleated move to a separate area of the dish and enucleate the rest of the oocytes. When you are ready to "reconstruct" (putting a cell into the enucleated oocyte), turn the UV light off, turn up the light to a comfortable level. Get an enucleated oocyte on the holder, using your tip, turn the oocyte until the "slit" made when enucleating the oocyte is in focus and in the same plane as your tip. Using the slit deposit one cell into the space between the zona and the cytoplasmic membrane of the oocyte to create a reconstructed embryo. Rinse all reconstructed embryos in TLHepes and then place into a maturation caffeine media (2 ml in vitro maturation media with 3.9 mg caffeine) until ready to fuse, at approximately 24 hours post maturation.

When ready to fuse (approximately at 23.5-24 hours post maturation), turn on the BTX machine (ECM Square Wave Electroporation System 830), making sure the settings are: mode LV, voltage 100, pulse length 40 µsec. Put the fusion chamber into the 100 mm dish, attach the red lead to the top wire, the black lead to the lower wire. Transfer reconstructed embryos in a dish comprising TLHepes. Pick up 8-10 reconstructed embryos and transfer to a dish containing a caffeine media (29.1 mg of caffeine in 15 ml of TLHepes) and let them sink. Transfer the 8-10 reconstructed embryos to another dish containing 2 ml of a SOR-based media (77.7 mg caffeine in 50 ml of SOR media) and let the sink. Finally, transfer the 8-10 reconstructed embryos to the fusion chamber, which is filled with the SOR-based media, and once the reconstructed embryos are lined up, hit "pulse" on BTX machine. Once fused, transfer reconstructed embryos back to the dish containing the caffeine media for rinsing and then to a dish containing TLHepes, until all reconstructed embryos are fused. When fusions are completed, transfer all fused embryos to a dish containing 500 µl of a CR1aa/CR2 media (comprising 9.7 mg caffeine/5 ml CR2) for 1 hour.

To activate, (at 25 hours, 1 hour post-CR2+caffeine), place reconstructed embryos in a nunc well along with 500 µl of ionomycin media (3 µl ionomycin and 3 ml TLHepes) for 4 minutes. Remove and rinse three times in a dish of warm TLHepes. Transfer the activated embryos to a nunc well containing 500 µl of cycloheximide media (at a concentration of 10 µg/ml of cycloheximide) and return to the incubator for 5 hours. After the 5 hours, remove the lysed oocytes, and rinse the remaining oocytes 6 times through the center area of the nunc well and return to the incubator. This is Day 0. On Day 5, move all embryos that are less than 8 cells to another nunc well, (count the number of 1 cells, cleaved, 8 cells and morula), leave the 8 cells and morula, add 25 µl of warm fetal bovine serum (FBS 5%) to the well and return to the incubator. On Day 6 and Day 7, check for any embryos that can be transferred. If there are, using a 2 ml Sartstedt tube, put 1 ml of Minitube holding media (BoviHold, Minitub International) into the tube and warm. Once the media is warm, transfer embryos to the tube and send to the farm for embryo transfer.

Increasing Genetic Progress in a Genetic Nucleus, Line or Herd Using Clones Generated from Embryonic or Fetal Cells Within a genetic nucleus, (or line or herd), once selected, parents that produce the next generation are mated with one another, while avoiding matings between closely related individuals, with the goal of increasing the genetic merit of the next generation. An increase in the genetic merit of the next generation constitutes genetic progress. An increase in genetic merit, in this context, means that for a given trait or set of traits, the individuals in the successive generation will express the desired trait or set of traits more strongly than their parents. With respect to undesirable traits, an increase in genetic merit means the individuals in the successive generation will express the trait or set of traits less strongly than their parents.

Genetic change, including desirable genetic change (i.e., genetic progress per year), ("dG") can be measured as the difference between the average genetic level of all progeny born in one year and all progeny born the following year. The difference is the result of selected parents having higher genetic merit than the average genetic merit of all the selection candidates (the animals available for selection as parents of the next generation). In ideal conditions, this depends upon the heritability ($h^2$) of the trait and the difference between the average performance of selected parents and that of selection candidates. The heritability of a trait ($h^2$) is the proportion of observable differences (phenotypic variance, $\sigma^2_P$) in a trait between individuals within a population that is due to additive genetic (A), as opposed to environmental (E), differences ($h^2=\sigma^2_A/\sigma^2_P=\sigma^2_A/(\sigma^2_A+\sigma^2_E)$). The difference between the average performance of selected parents and that of all selection candidates (of which the selected parents are a subset) is also known as the selection differential.

The genetic progress per year is the result of genetic superiority of selected males and of selected females. This is expressed in the following equation:

$$dG=\{(R_{IH}*i)_{males}+(R_{IH}*i)_{females}\}*\sigma_H/(L_{males}+L_{females}),$$

Where, R=the accuracy of selection, i=the selection intensity, $\sigma_H$=genetic variation and L=generation interval, for male or female parents.

H=breeding goal that combines genetic merit (g) of the traits (1 to m) that need to be produced weighted by the economic values (v) of the traits ($H=v_1g_1+v_2g_2+ \ldots +v_mg_m$). The economic value is positive if selection is for larger phenotypic values and negative if selection is for smaller phenotypic values.

I=an index that combines all the trait information on the individual and its relatives and is the best estimate of the value of H for the individual.

In a large population, the selection intensity depends upon how many animals are tested and how many are selected—the lower the proportion selected the higher the selection intensity and the larger the genetic progress, all else being equal. Thus, in order to maximize genetic progress, one should rank all tested animals based on the GEBV, for example, and then select the minimum number of top males and females required to maintain the line, breed and/or herd size and to avoid inbreeding problems. This ensures that the average GEBV of selected animals is substantially higher than the average GEBV of all animals tested. In particular through the use of AI, one needs to select fewer males than females and the selection intensity for males is higher than for females.

The generation interval for males (or females) is the average age of male parents (or female parents) when progeny are born. The annual rate of genetic progress depends on the generation interval and on the superiority of the parent's GEBVs compared to that of the selection candidates. In general, males contribute more to the genetic progress per year than the females.

"Line" as used herein refers to animals having a common origin and similar identifying characteristics. "Genetic nucleus" as used herein refers to one or more populations of male and female animals used to generate selection candidates in a breeding program. "Breeding program" as used herein refers to a system for making genetic progress in a population of animals.

The invention encompasses a method in which GEBVs for a population, which may include a genetic nucleus, line or herd, are obtained from DNA extracted from embryonic or fetal cells isolated from allantoic fluid or from DNA extracted from the allantoic fluid itself, rather than from tissue samples obtained from adults. The method generally encompasses the steps of extracting DNA from embryonic or fetal cells of an embryo or fetus from the population; genotyping the DNA to obtain a genotype for the embryo or fetus; determining a GEBV of the embryo or fetus based on the genotype; selecting the embryo or fetus as a parent for the population based on the GEBV; and cloning the embryo or fetus to produce a clone. By determining the genetic merit of an embryo or fetus early in gestation, a breeder is able to increase the number of selection candidates available to select from over time, because pregnancies of recipient females involving low genetic merit embryos or fetuses can be terminated and the recipient females (whose numbers are limited) can be more quickly recycled to receive another selection candidate. Such an increase in the production of selection candidates in a population increases selection intensity and consequently the rate of genetic progress. Furthermore, the use of cloning independently results in a decrease in the number of selected animals and thereby increases selection intensity and genetic progress. This is because multiple copies of a single female parent with a superior genomic score can be used to produce all, or a larger portion, of the required number of replacement heifers for the next generation (as opposed having to select multiple different females in order to produce a sufficient number of replacements). In certain embodiments of the invention, after determining a GEBV (or GPTA) of an embryo or fetus using cells or fluid obtained from within the embryo's or fetus's allantois, the embryo or fetus is permitted to continue gestating within the female recipient based on the determined GEBV, and the female recipient is subjected to a second procedure to obtain amniotic fluid or cells from within the amnion of the gestating embryo or fetus. Cells or amniotic fluid obtained during this second procedure can be used generate another GEBV for the embryo or fetus. Cells obtained during this second procedure can also be used to generate a cell culture or to clone the embryo or fetus.

Once produced, cloned females can be used as parents for the next generation using OPU and IVF, including superovulation. Thereafter, the above steps can be repeated, i.e., embryos resulting from IVF, once transferred into recipients, can be genomically evaluated using their amniocytes and a determination can be made whether they will be parents and thus cloned, or alternatively, aborted.

In certain aspects of this embodiment, it is contemplated that IVF is performed using sex-sorted sperm. The term "sex-sorted sperm" includes a sperm sample that has been processed to skew the ratio of X-bearing chromosome sperm to Y-bearing chromosome sperm. As contemplated herein, "sex sorted sperm" can be created either by separating X- and Y-bearing sperm from one another via, for example, well known techniques using flow cytometry, or alternatively, by killing or otherwise incapacitating sperm bearing the undesired sex chromosome via, for example, laser ablation. In certain embodiments, at least 60%, 70%, 80%, 90%, 98% or 99%, of sperm in a sex-sorted sperm sample, bear an X-chromosome. In other embodiments, at least 60%, 70%, 80%, 90%, 98% or 99%, of sperm in a sex-sorted sperm sample, bear a Y-chromosome.

EXAMPLE 37 bovine embryos (2 Jersey embryos and 35 Holstein embryos) were generated via i) IVF or ii) AI involving synchronized supernumerary follicle production and scheduled non-surgical transvaginal catheterized intrauterine embryo recovery.

Production of embryos via IVF utilized the following procedure. Prophase I immature COCs were recovered from peripubertal Holstein heifers using a TVOR system. The immature COCs were brought into the laboratory and placed into an IVM culture system. After an overnight culture period, oocytes that progressed through meiosis I and were morphologically normal, were used in IVF. The mature oocytes were placed into IVF drops and fertilized with a specific concentration of capacitated sperm from a Holstein bull. Zygotes (day 1) were placed into traditional co-culture system and cultured to uterine stages of development by day 7-8 of culture.

All 37 embryos were transported to a recipient heifer farm where they were non-surgically transferred into a synchronized recipient females. The pregnancy was monitored on a regular and scheduled basis via transrectal real time ultrasonography.

33 to 66 days after conception of each of the embryos, allantoic fluid was collected from the respective recipient female. See FIG. 1. The recipient female was restrained in stocks and sedated prior to performing collection of allantoic fluid. The recipient's rectum was emptied of feces, and under epidural anesthesia, the vulva and rectal area of the recipient was cleaned and scrubbed. The disinfection step was completed by rinsing the vulva and rectal area with Betadine solution and then rinsing and spraying the cleaned area with 70% ethanol. TVOR equipment was cleaned and sterilized with ethanol immediately prior to its introduction into the vagina and was fitted with a sterile stainless steel single-needle guide. The TVOR equipment was advanced into the vagina, positioned to the left or the right of the cervical os and by means of manipulation per rectum, the pregnant uterine horn was positioned against the probe, avoiding interposition of other tissue in the proposed needle path. The exact location of the allantois was determined by the recognition of embryo body parts, the allantoic, amniotic and chorionic membranes, and the uterine wall. When a non-echogenic area representing allantoic fluid was seen on the monitor screen, a sterile needle with a stylette was inserted within the needle guide and advanced penetrating through the vaginal wall, uterus and subsequent fetal membranes. As soon as the tip of the needle was seen to have entered the fetal fluid compartment, the stylette was withdrawn from the needle and the needle was placed inside the allantois of the fetus. An initial amount of allantoic fluid was aspirated into the tubing and flushed out of the tubing system to reduce or eliminate maternal contamination. Then, using a sterile syringe, an additional 10-45 ml of allantoic fluid was aspirated from each allantois. See FIG. 1. During the fluid collection, the pregnant uterine horn was held in the same position, and the exact location of the tip of the needle was guaranteed by its visualization on the ultrasound screen. The syringe containing the collected fluid was placed on ice and transported back to the laboratory for genomic analysis.

An equal volume of a solution containing Tris-EDTA was added to each cell sample. The cell suspension was then stored in 1.5 ml microcentrifuge tubes at 4° C. until required for DNA extraction. The 1.5 ml tubes containing cell suspension were spun at ≥10000×g in a microcentrifuge for 45 seconds to pellet the cells. The suspension solution was pipetted off carefully so as to not remove the pelleted cells. Approximately 50 μl of suspension solution was left in each tube. The tubes were then vortexed for 10 seconds to resuspend the cell pellets. 300 μl of Tissue and Cell Lysis Solution (Epicentre; Madison Wisconsin; Catalog #MTC096H) containing 1 μl of Proteinase K (Epicentre; Madison Wisconsin; at 50 ug/μ1; Catalog #MPRK092) was then added to each tube and mixed. The tubes were incubated at 65° C. for 30 minutes and vortexed at 15 minutes. The samples were cooled to 37° C. Afterwards 1 μl of 5 mg/μl RNase A (Epicentre; Madison Wisconsin; at 5 mg/ml; Catalog #MPRK092) was added to each sample and then mixed. The samples were then incubated at 37° C. for 30 minutes. The samples were then placed in a 4° C. cooler for 5 minutes. 175 μl of MPC Protein Precipitation Reagent (Epicentre; Madison Wisconsin; Catalog #MMP095H) was added to each sample, and the samples vortexed vigorously for 10-15 seconds. The samples were centrifuged in order to pellet debris for 8 minutes at ≥10000×g. The supernatant was transferred to a clean microcentrifuge tube. 600 μl of cold (−20° C.) isopropanol was added to the supernatant. Each tube was then inverted 30-40 times. The DNA was pelleted by centrifugation for 8 minutes in a microcentrifuge at ≥10000×g. The isopropanol was poured off without dislodging the DNA pellet. The pellet was rinsed once with 70% ethanol and then the ethanol was carefully poured off so as not to disturb the DNA pellet. The residual ethanol was removed with a pipet, and the DNA pellet was allowed to air dry in the microcentrifuge tube. Once dried, the DNA pellet was resuspended in 20 μl Tris-EDTA.

The extracted DNA was then genotyped using Illumina bovine SNP BeadChips. The data generated by the SNP BeadChips were used to confirm parentage of the donor embryos and yielded a Genomic Total Performance Index® (GTPI®) score for each of the Holstein embryos, with GTPI® values ranging between 2128 and 3056. For the two Jersey embryos, JPI scores of 120 and 146 were generated for each one, respectively. For the genotypes that generated GTPI or JPI scores, call rates were 95% or higher. Three of the 37 embryos failed to generate genomic scores due to low call rates. See FIG. 1.

Although the foregoing invention has been described in some detail, one of ordinary skill in the art will understand that certain changes and modifications may be practiced within the scope of the claims.

What I claim is:

1. A method of increasing the rate of genetic progress in a non-human mammalian population comprising obtaining one or more embryonic or fetal cells from within an allantois of an embryo or a fetus gestating within a female within 60 days of the embryo's or fetus's conception;

extracting DNA from the one or more embryonic or fetal cells;

genotyping the extracted DNA to obtain a genotype for the embryo or fetus, wherein call rates for the genotype are greater than 80%;

determining a genomic estimated breeding value (GEBV) or a genomic predicted transmitting ability (GPTA) using the genotype; and selecting the embryo or fetus as a parent, or to produce gametes, based on the determined GEBV or GPTA.

2. The method of claim 1, wherein the one or more embryonic or fetal cells are obtained from the allantois within 50 days of the embryo's or fetus's conception.

3. The method of claim 2, wherein the one or more embryonic or fetal cells are obtained from the allantois within 40 days of the embryo's or fetus's conception.

4. The method of claim 1, wherein the one or more embryonic or fetal cells are obtained from the allantois 28 to 60 days after the embryo's or fetus's conception.

5. The method of claim 4, wherein the one or more embryonic or fetal cells are obtained from the allantois 30 to 40 days after the embryo's or fetus's conception.

6. The method of claim 5, wherein the one or more embryonic or fetal cells are obtained from the allantois 30 to 35 days after the embryo's or fetus's conception.

7. The method of claim 1, further comprising a step of culturing the one or more embryonic or fetal cells.

8. The method of claim 1, further comprising a step of cloning the embryo or fetus using one of the one or more embryonic cells or fetal cells.

9. The method of claim 1, wherein call rates for the genotype are greater than 90%.

10. A method of increasing the rate of genetic progress in a non-human mammalian population comprising obtaining allantoic fluid from within an allantois of an embryo or a fetus gestating within a female within 60 days of the embryo's or the fetus's conception;

extracting DNA from the allantoic fluid;

genotyping the isolated DNA to obtain a genotype for the embryo or fetus, wherein call rates for the genotype are greater than 80%;

determining a genomic estimated breeding value (GEBV) or a genomic predicted transmitting ability (GPTA) using the genotype; and selecting the embryo or fetus as a parent, or to produce gametes, based on the determined GEBV or GPTA.

11. The method of claim 10, wherein the allantoic fluid is obtained from the allantois within 50 days of the embryo's or fetus's conception.

12. The method of claim 11, wherein the allantoic fluid is obtained from the allantois within 40 days of the embryo's or fetus's conception.

13. The method of claim 10, wherein the allantoic fluid is obtained from the allantois 28 to 60 days after the embryo's or fetus's conception.

14. The method of claim 13, wherein the allantoic fluid is obtained from the allantois 30 to 40 days after the embryo's or fetus's conception.

15. The method of claim 14, wherein the allantoic fluid is obtained from the allantois 30 to 35 days after the embryo's or fetus's conception.

* * * * *